United States Patent [19]
Schwab, Jr.

[11] Patent Number: 5,192,932
[45] Date of Patent: *Mar. 9, 1993

[54] SENSING MAT, AND METHODS OF CONSTRUCTING AND UTILIZING SAME

[76] Inventor: Henry J. Schwab, Jr., 429 Rittenhouse Cir., Havertown, Pa. 19083

[*] Notice: The portion of the term of this patent subsequent to Feb. 4, 2009 has been disclaimed.

[21] Appl. No.: 694,510

[22] Filed: May 2, 1991

Related U.S. Application Data

[63] Continuation-in-part of Ser. No. 430,146, Nov. 1, 1989, Pat. No. 5,086,291.

[51] Int. Cl.$^5$ .............................. G08B 21/00
[52] U.S. Cl. ........................... 340/604; 324/693; 340/693
[58] Field of Search .................. 340/604–605, 340/573, 562, 571, 693, 310 A, 333; 604/361; 128/886; 324/664, 689, 693–694; 200/61.05

[56] References Cited

U.S. PATENT DOCUMENTS

| | | |
|---|---|---|
| 2,127,538 | 8/1938 | Seiger . |
| 3,460,123 | 8/1969 | Bass .................. 340/573 |
| 3,986,110 | 10/1976 | Overall et al. . |
| 4,083,038 | 4/1978 | Iclebanoff . |
| 4,163,449 | 8/1979 | Regal .................. 128/886 |
| 4,191,950 | 3/1980 | Levin et al. .......... 340/604 |
| 4,212,295 | 7/1980 | Snyder ................ 128/886 |
| 4,297,686 | 10/1981 | Tom .................. 340/604 |
| 4,319,232 | 3/1982 | Westphal et al. ..... 340/604 |
| 4,356,881 | 11/1982 | Macias et al. ....... 128/886 |
| 4,688,027 | 8/1987 | Widener ............. 340/604 |
| 4,896,052 | 1/1990 | Morrison et al. . |
| 5,086,291 | 2/1992 | Schwab, Jr. ........ 340/604 |

FOREIGN PATENT DOCUMENTS

| | | | |
|---|---|---|---|
| 2145859 | 4/1985 | United Kingdom ..... 340/604 |
| 8401626 | 4/1984 | World Int. Prop. O. .. 128/886 |

Primary Examiner—Jin F. Ng
Assistant Examiner—Thomas J. Mullen, Jr.
Attorney, Agent, or Firm—Irving M. Weiner; Robert M. Petrik; Joseph P. Carrier

[57] ABSTRACT

A device for sensing the presence of liquids or other substances and warning of potential hazards. The device includes a mat which is constructed of metalized sheets. This mat may be cut to any size or shape on site. A monitoring device is electrically connected to the mat and monitors a change in capacitance or resistance of the mat. Such a change is an indication of the presence of unwanted substance. The monitoring device may then either activate an alarm or turn off any electrical devices as deemed necessary. The mat can include a sensitivity layer which may be included to require a greater amount of liquid or other substances to trip the monitoring device. The control module preferably operates on a large range of power voltages, preferably the same as the equipment being monitored.

17 Claims, 5 Drawing Sheets

SENSING MAT, AND METHODS OF CONSTRUCTING AND UTILIZING SAME

CROSS REFERENCES TO RELATED APPLICATION

This is a continuation-in-part application of U.S. Ser. No. 430,146 filed Nov. 1, 1989, now U.S. Pat. No. 5,086,291.

BACKGROUND OF THE INVENTION

1. Field of the Invention

The present invention relates to warning or alarm systems and, more particularly, to an electrical device of variable size for use in signalling the presence of unwanted substances such as liquids near sensitive electrical equipment.

The electrical device comprises a mat of variable dimensions, including width, length, and variable sensitivity, specifically adapted to signal the presence of water adjacent electrical equipment such as air conditioning equipment. The device includes a control module which can operate on a range of voltages and includes an audible and/or visual alarm.

2. Description of the Relevant Art

Heretofore, there have been various means for signalling the presence of liquids. In the heating and air conditioning industry, it has been known to provide a collection pan with a float switch therein for turning off equipment which may be damaged by the presence of water. A disadvantage to this method is that enough water must collect in the pan to activate the floatswitch.

U.S. Pat. No. 2,127,538 discloses a device for use in determining the presence of moisture in a child's bed. A series of wires are provided on a mat. When moisture contacts two wires, a relay switch is closed and an alarm, either audible or visual, will be activated.

This device cannot be varied in size since cutting of the device can result in the cutting of wires and destruction of the device.

U.S. Pat. No. 3,986,110 discloses a device for determining the depth of a liquid accumulating on its surface. The device is constructed of a non-conductive material with a web of elongated strips of foil. The device operates such that the presence of liquid affects the capacitance and conductance of the sensor.

Again, this device cannot be adapted to situations other than that discussed above.

U.S. Pat. No. 4,083,038 discloses a sensor for determining the level of a liquid in a container. The device employs a web of non-conductive material with electrically conducting plates spaced therein. As the liquid level in the container drops, the capacitance of the device changes to cause an alarm to be given.

The present invention provides a device capable of being sized and shaped for the given situation on site. In addition, the device is lightweight and easily transportable.

SUMMARY OF THE INVENTION

The present invention provides a readily adaptable, sensitive alarm or warning system. The system comprises a mat made of sheets including a conductive and non-conductive side and an electronic circuit monitor to check the resistance or the capacitance of the mat.

In a preferred embodiment, the mat comprises at least two sheets of "metalized" material, such as MYLAR sheets. Each sheet of this material must include a conductive side and non-conductive side. One sheet will include a pattern of apertures therethrough. The two sheets will be laminated together to form the mat. This mat may then be cut to any size or shape.

The circuit monitor may be attached to this mat by electrical leads. When unwanted material, either liquid, powder or metal shavings, contacts the mat in sufficient quantity to cause a change in resistance or capacitance of the mat, an alarm and/or switch is activated.

It is an object of the present invention to provide an alarm system which is readily adaptable to any situation.

It is a further object of the present invention to provide a lightweight, easily transportable device.

It is still a further object of the present invention to provide a mat which is flexible and can be cut to any size and the sensitivity is determined by the pattern configurations provided.

It is a further object of the present invention to provide a mat having a pattern of conductive material screened onto a non-conductive sub-surface.

It is a further object of the present invention to provide an electronic control module having an audible or visual indicator and control of the operation of the equipment being monitored.

The above and further objects, details and advantages of the invention of the invention will become apparent from the following detailed description, when read in conjunction with the accompanying drawings.

DETAILED DESCRIPTION OF THE PREFERRED EMBODIMENT

Figure 1:
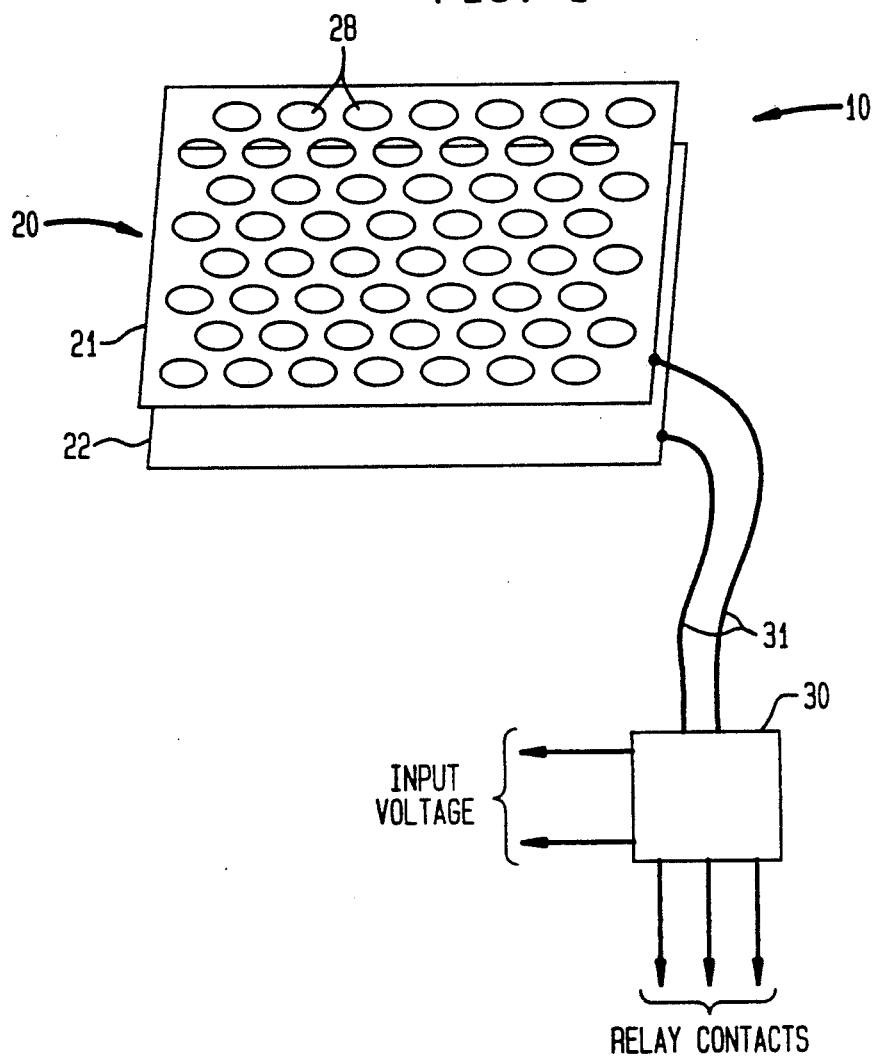
FIG. 1 illustrates an alarm/switch system in accordance with the present invention.

As shown in FIG. 1, the alarm/switch system 10 includes a thin, flexible mat 20 and monitoring circuit 30. The mat 20 is electrically connected to the monitoring means or circuit 30 by means such as leads 31. The leads 31 may be electrically connected to the mat by any known means including soldering. The leads 31 must be connected to the conductive sides of each sheet layer 21, 22.

Figure 2:
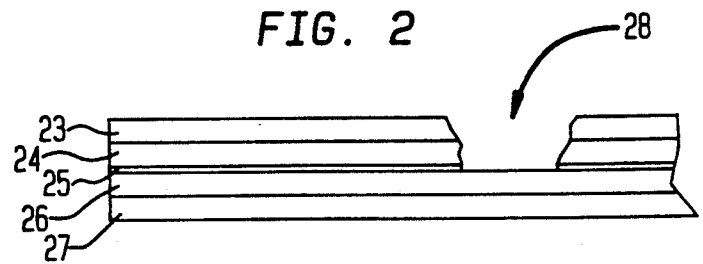
FIG. 2 illustrates a partial cross-section of a mat in accordance with the present invention.

Upper sheet 21 includes a pattern of apertures 28 therein. As best seen in FIG. 2, sheet 21 includes a conductive side 23 and non-conductive side 24. Conductive side 23 may include any type of well-known conductive material. Non-conductive side 24 may be paper, plastic or any other well-known insulative material. Side 24 must always be adjacent conductive side 26 of sheet 22. Preferably, the sheets 21, 22 are MYLAR (or any similar material).

Lower sheet 22 includes a conductive side 26 and preferably a non-conductive side 27.

Sheets 21, 22 are joined together by adhesive 25. Adhesive 25 does not entirely cover lower sheet 22 since the aperture 28 must permit unwanted substances to reach conductive layer 26.

Aperture 28 may comprise any pattern of holes, slots or slits or any combination thereof.

Monitoring means 30 is connected to a power source or voltage input and relay contacts which may turn off the electrical equipment or activate an alarm.

In use, a large sheet of mat 20 may be brought to the required location. Generally, the mat will be located where electrical or other sensitive equipment may be harmed by water or other unwanted substances. The device may also be employed wherever it is desired to prevent property damage.

Mat 20 may be cut to the desired size and shape. This flexibility permits the mat to be retrofitted to locations normally inaccessible to known sensors. The mat 20 may be placed in conjunction with a screen or grill 40 to insulate it from vibrational damage which may be caused by an electric motor and prevent it from shorting out by conductive materials placed on it.

Once the leads 31 are attached to the mat 20, the monitor 30 will observe either the capacitance or the resistance of the mat. When a liquid or other material contacts the mat 20 and can contact both sheets 21, 22 or, in other words, conductive sides 26, 23, a shorted capacitance or lower resistance will result.

Upon sensing one of the changes set forth above, the monitoring circuit 30 may set off an alarm or turn the equipment off to prevent any damage.

Figure 3:
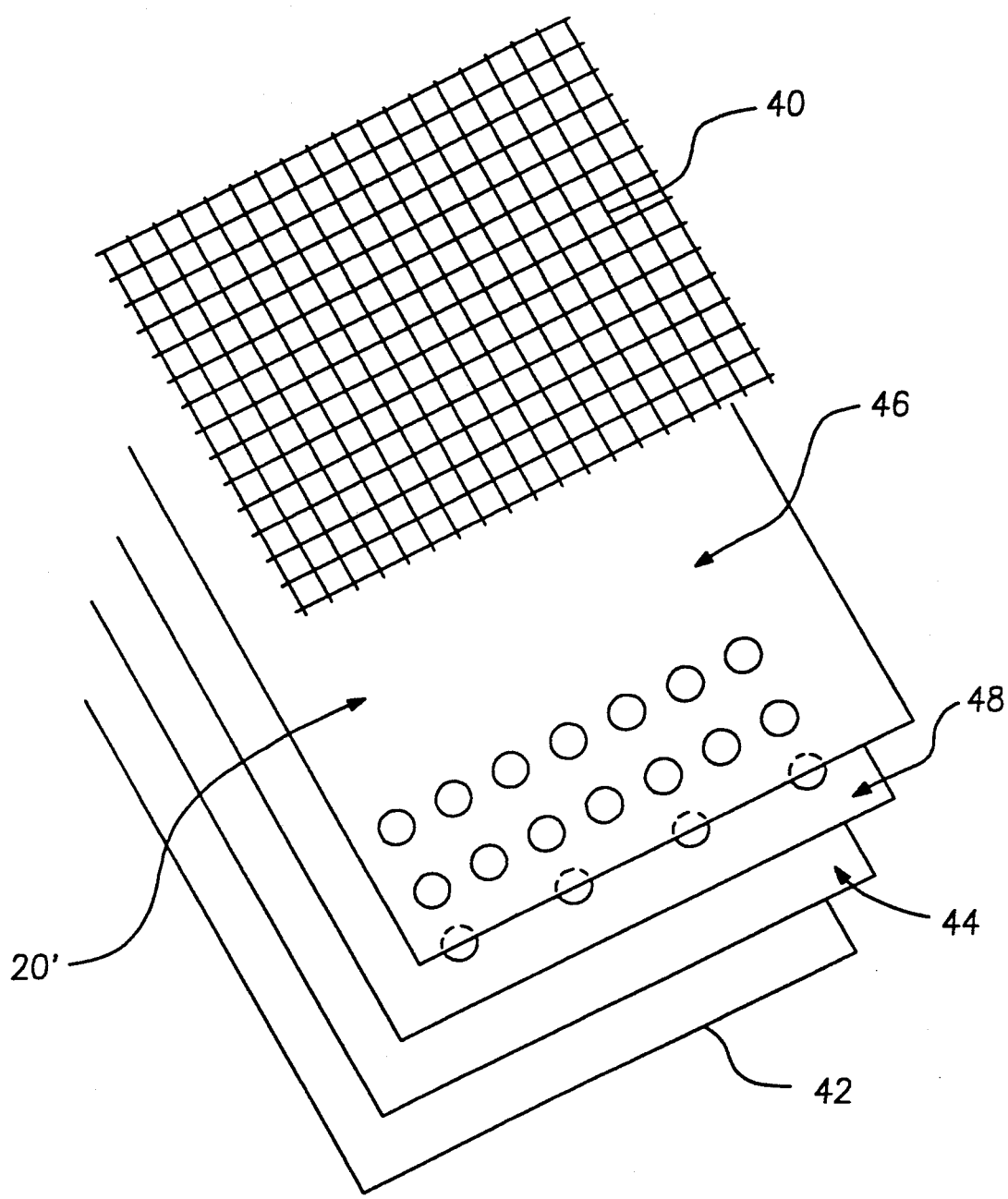
FIG. 3 illustrates a second embodiment of the mat in accordance with the present invention.
Figure 5:
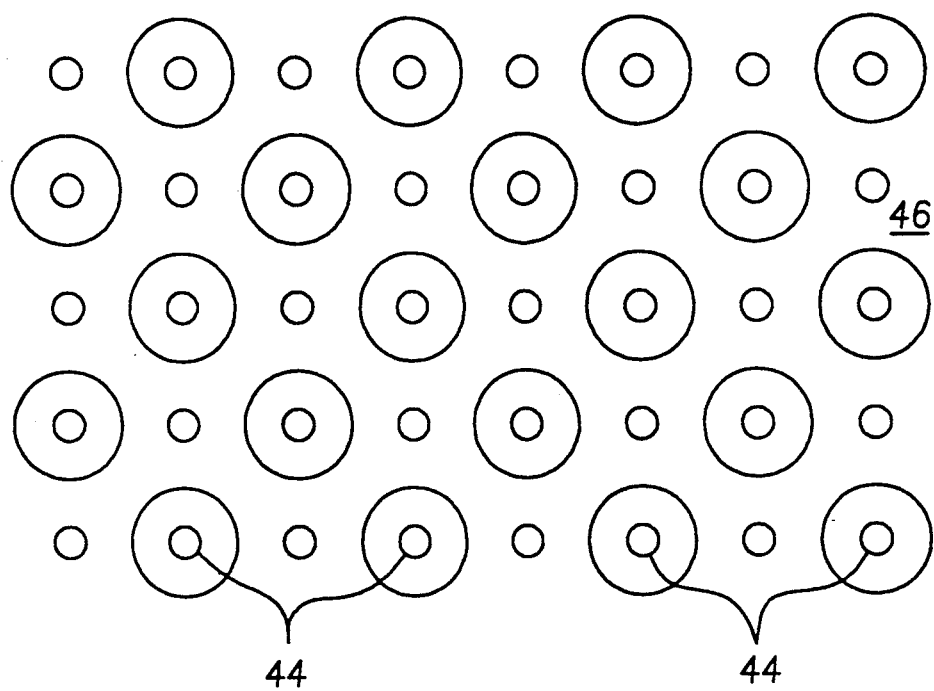
FIG. 5 illustrates a top view of the mat as shown in FIG. 3.

As seen in FIGS. 3 and 5, a mat 20' may have at least one additional layer or outer layer 46 of different designed patterns to adjust the sensitivity of the mat. A greater volume of liquid would be required to permit the liquid to contact sheets 21, 22 and thus the alarm or monitor 30 is not as easily tripped. This additional layer 46 may also provide a physical outer protection for the mat 20'. Outer layer 42 may be added to the mat 20 shown in FIGS. 1 and 2.

Referring now specifically to FIG. 3, the mat 20' is composed of an outer layer 42, a bottom metallized sheet 44 adjacent the outer layer 42, a first sheet 48 similar to sheet 21 in FIG. 1 and a sensitivity layer 46 including a pattern of apertures. The sensitivity layer 46 provides a greater space between the exposed conductive surface of sheet 48 and the exposed conductive bottom metallized sheet 44. Thus, a greater volume of liquid is required to change the resistivity or capacitance of the monitored sheets to indicate the presence of the liquid or other unwanted material. A top screen 40 may be provided in conjunction with this embodiment as discussed above. As shown by the pattern, sensitivity layer 46 may be provided to adjust the sensitivity of the mat 20'. A sensitivity layer 46 may be laminated to the sheets of mat 20 of FIGS. 1 and 2.

Figure 4:
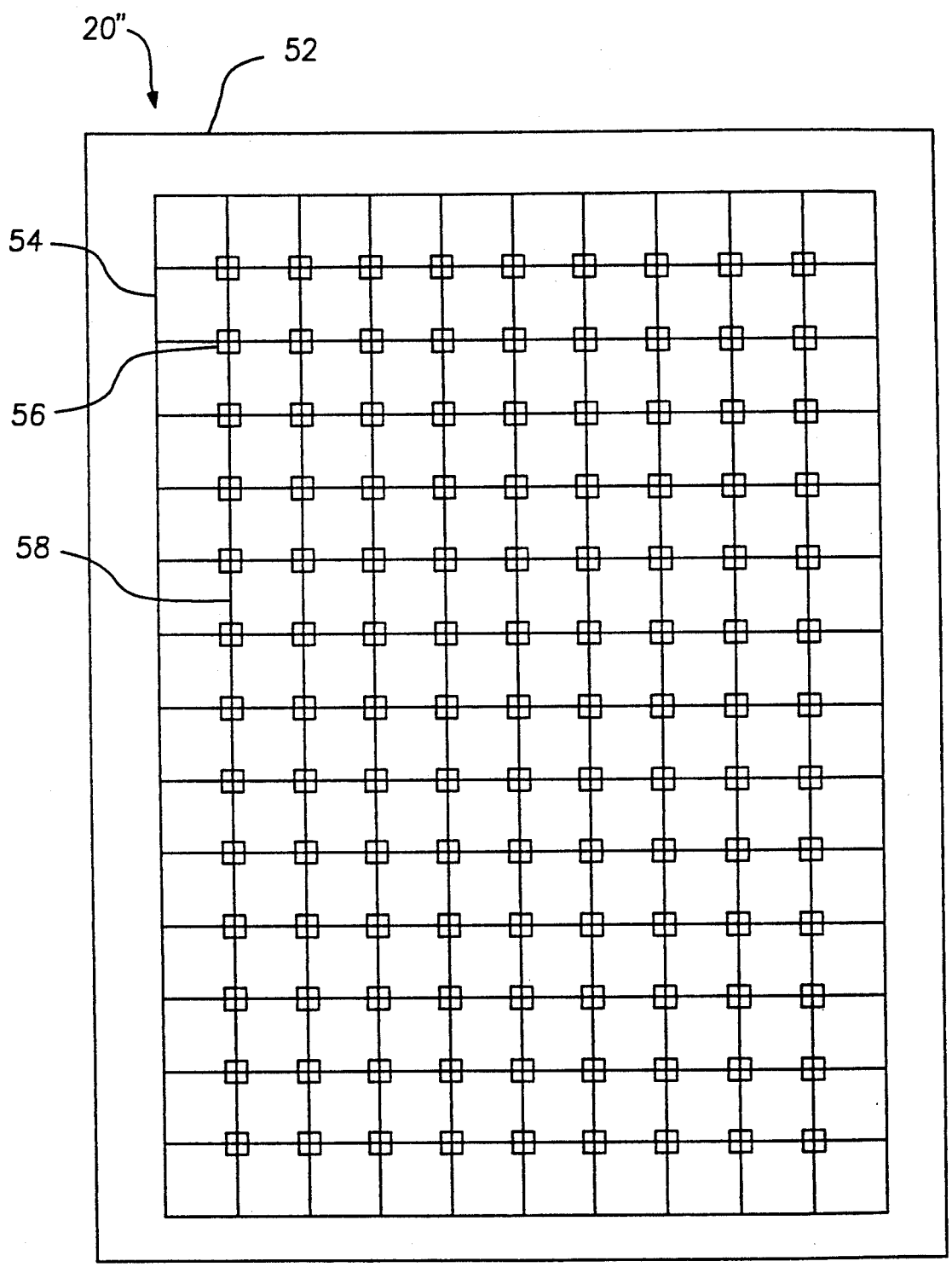
FIG. 4 illustrates a third embodiment of the mat in accordance with the present invention.

Shown in FIG. 4 is a top view of a third embodiment of a mat 20" in accordance with the present invention. The mat 20" is constructed by utilizing a screening (or painting, etching, etc.) process to provide a pattern of conductive and non-conductive. The process encompasses the painting of a conductive "ink" 54 onto a non-conductive base 52. A non-conductive material 56 would be "screened" or added at the intersecting points of the ink 54. The second conductive ink pattern 58 is screened on with the non-conductive material 56 acting to prevent the two patterns 54, 58 from short circuiting. When liquid contacts both conductive ink patterns, the alarm would be activated.

Figure 6:
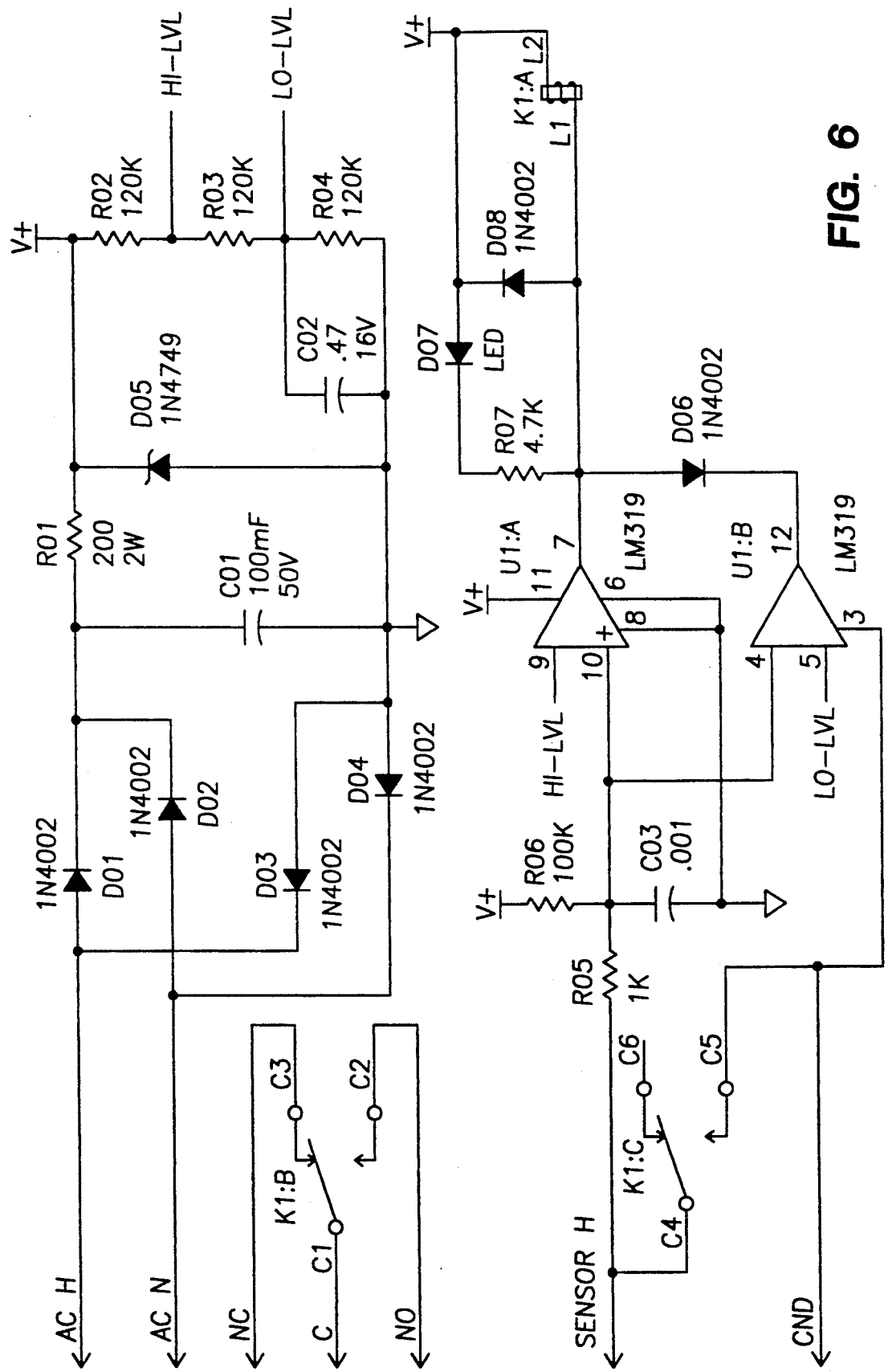
FIG. 6 illustrates a schematic for the electronic control module in accordance with the present invention.

Referring now to FIG. 6 a schematic 60 for the electronic control module 30 is shown. The module 30 is preferably employed in accordance with mat 20. However, module 30 will monitor any change in resistance or capacitance from any leads 31. Such leads 31 may even comprise two bare wires.

The module 30 is preferably adapted to operate on the same voltage as the equipment the sensing mat 20 is monitoring. This eliminates the need for additional wiring for the power sources. For example, in the heating and air conditioning industry, the equipment generally operates on 24 volts AC.

The module 30 provides a supervised sensing means capable of providing an audible alarm, visible alarm or automatic shut off of the equipment upon sensing the presence of an unwanted material such as water. Preferably, the module 30 communicates with or controls a circuit for deactivating the monitored equipment and requires the manual reset of the control circuit for activation of the equipment. This insures that the equipment will not be operated under dangerous or unwanted conditions.

Referring now specifically to the schematic of FIG. 6, the power supply includes a rectifier bridge, zener regulator and associated filtering and protection apparatus to permit acceptance of AC or DC input.

The supervision circuit preferably consists of a 100K ohm resistor in the sensor with a 100K ohm pull-up resistor to the voltage supply. During normal conditions, these two resistors form a one-half voltage divider which provide 12 volts to the voltage comparitor. An open condition (or short) in the sensor will trip the voltage comparator.

A feedback path from the output of the voltage comparator to its negative input creates a latching effect which keeps the comparitor tripped even if the condition of the sensor returns to normal. Power must be removed in order to reset the "latch". The open condition controls a control relay which is used to deactivate the monitored equipment.

The invention is characterized by simplicity, economy of manufacture, durability and convenience of use. Its compactness and ready adaptability to any situation renders the invention practical where the prior art has proved to be impractical.

Although there has been described what is at present considered to be preferred embodiments of the invention, it will be understood that various modifications and variations may be made therein, and it is intended to cover, in the appended claims, all such modifications as fall within the true spirit and scope of the invention.

I claim:

1. A warning device for the prevention of damage to electrical equipment and property by liquids, comprising:

a thin, flexible mat which is adaptable to various situations by changing the size to meet the required conditions on site including conductive and non-conductive portions;

a sensitivity layer for adjusting the sensitivity of said mat;

a monitoring means for sensing changes in the electrical properties of said mat;

means to electrically connect said mat to said monitoring means;

upon sensing a change in the electrical properties of said mat, a warning device is activated by said monitoring means;

said monitoring means deactivates said electrical equipment; and said mat may be cut to change the size and shape.

2. The device of claim 1, wherein:

said mat is adaptable to various situations by changing the size to meet the required conditions on site; and said device further comprising an outer layer to provide physical protection to said mat.

3. The device of claim 1, wherein:

said mat comprises two layers of metalized sheets and said sensitivity layer is provided in various patterns to adapt the mat to particular circumstances.

4. The device of claim 3 wherein:

each said layer includes a conductive side and a non-conductive side.

5. The device of claim 4, wherein:

said two layers includes an upper layer and lower layer; and said upper layer includes a pattern of apertures therein.

6. The device of claim 1, wherein:

said monitoring means may deactivate said electrical equipment such that manual reset of said equipment is required.

7. A warning device for the prevention of damage to property such as electrical equipment, comprising:

a thin, flexible mat including conductive and non-conductive portions;

said mat comprises two layers of metalized sheets and a sensitivity layer therebetween;

each said layer of metalized sheets include a conductive side and a non-conductive side;

said two layers of metalized sheets includes an upper layer and lower layer, said upper layer includes a pattern of apertures therein;

said upper layer conductive side is facing downward;

said lower layer conductive side is facing up and is adjacent said upper non-conductive side;

a monitoring means for sensing changes in the electrical properties of said mat;

means for electrically connect said mat to said monitoring means; and upon sensing a change in the electrical properties of said mat, a warning device is activated by said monitoring means.

8. The device of claim 7, wherein:

said upper layer conductive side and said lower layer conductive side are electrically connected to said monitoring means by said means to electrically connect.

9. The device of claim 8, wherein:

said monitoring means senses a change in capacitance of said mat.

10. The device of claim 9, wherein:

a change of capacitance of said mat results from an unwanted substance contacting both said upper and lower conductive sides via said apertures.

11. The device of claim 10, wherein:

said change in capacitance results in a warning device being activated.

12. The device of claim 8, wherein:

said monitoring means senses a change in resistance of said mat.

13. The device of claim 12, wherein:

a change of resistance of said mat results from an unwanted substance contacting both said upper and lower conductive sides via said apertures.

14. The device of claim 13, wherein:

said change in resistance results in a warning device being activated.

15. The device of claim 8, wherein:

said upper layer and lower layer are laminated to form an integral mat.

16. The device of claim 7, wherein:

said monitoring means comprises a control module adapted to operate on a wide range of input power voltages.

17. The device of claim 7, wherein:

said thin, flexible mat includes a conductive ink pattern painted on a non-conductive base.

* * * * *

UNITED STATES PATENT AND TRADEMARK OFFICE
CERTIFICATE OF CORRECTION

PATENT NO. : 5,192,932
DATED : March 9, 1993
INVENTOR(S) : Schwab, Jr.

It is certified that error appears in the above-indentified patent and that said Letters Patent is hereby corrected as shown below:

On the title page, in the References Cited Section, please change "4,356,881" to --4,356,818--.

Signed and Sealed this

Thirtieth Day of November, 1993

Attest:

BRUCE LEHMAN

Attesting Officer

Commissioner of Patents and Trademarks